United States Patent [19]

Lim et al.

[11] 4,217,275

[45] Aug. 12, 1980

[54] β-LACTAM ANTIBIOTIC ESTERIFICATION PROCESS USING METHOXYMETHYL METHANE SULFONATE

[75] Inventors: Gary M. F. Lim, Candiac; Roberto D. Droghini, St-Leonard, both of Canada

[73] Assignee: Bristol-Myers Company, New York, N.Y.

[21] Appl. No.: 16,238

[22] Filed: Feb. 28, 1979

[51] Int. Cl.$^2$ ............... C07D 499/08; C07D 501/02
[52] U.S. Cl. ............... 260/239.1; 260/245.2 R; 544/16; 544/18; 544/19; 544/20; 544/21; 544/22; 544/24; 544/25; 544/26; 544/27; 544/28; 544/29; 544/30
[58] Field of Search ............... 260/239.1, 306.76, 245.2; 544/18, 19, 20, 25, 27, 28, 24, 26, 29, 30, 16, 21, 22

[56] References Cited

U.S. PATENT DOCUMENTS

| | | | |
|---|---|---|---|
| 3,737,447 | 6/1973 | Mazur et al. | 260/456 R |
| 3,843,639 | 10/1974 | Sapino et al. | 544/18 |
| 3,996,236 | 12/1976 | Sleezer et al. | 260/306.7 C |
| 4,125,716 | 11/1978 | Crast et al. | 544/28 |

FOREIGN PATENT DOCUMENTS 1488308  10/1977  United Kingdom .................. 260/239.1

OTHER PUBLICATIONS

J. Am. Chem. Soc., 91, 5663, (1969).
Fed. Regist., 39, 1910, 93h, (Jan. 1974).
I Synthesis, Apr. 1975, p. 276.
II Synthesis, Apr. 1976, p. 244.
III Synthesis, Aug. 1977, p. 567.

*Primary Examiner*—Natalie Trousof
*Assistant Examiner*—Vera C. Clarke
*Attorney, Agent, or Firm*—David M. Morse

[57] ABSTRACT

Disclosed is an improved process for esterifying carboxylic acids, particularly 3-carboxylic acid groups of penicillins and 4-carboxylic acid groups of cephalosporins, to form methoxymethyl esters. Replacement according to the present process of the conventional halomethyl methyl ether esterifying agent with methoxymethyl mesylate avoids the carcinogenicity problem of the prior art reagent while still giving good yields of high quality product.

4 Claims, No Drawings

β-LACTAM ANTIBIOTIC ESTERIFICATION PROCESS USING METHOXYMETHYL METHANE SULFONATE

BACKGROUND OF THE INVENTION

1. Field of the Invention

The present invention relates to a new and improved process for esterifying an organic carboxylic acid, particularly a complex acid of the β-lactam type, to form the corresponding methoxymethyl ester. More particularly, it relates to the use of methoxymethyl methanesulfonate (methoxymethyl mesylate) as the esterifying agent in the methoxymethylation of a carboxylic acid group, especially the 3-carboxyl group of a penicillin or the 4-carboxyl group of a cephalosporin.

2. Description of the Prior Art

There is a growing need for esterification processes which can be applied to the manufacture of β-lactam antibiotics such as the penicillins and cephalosporins. It is frequently necessary to protect carboxylic acid groups in such molecules so as to enable chemical transformations to be carried out elsewhere in the molecule. Due to the known instability of the penicillins and cephalosporins, however, it is necessary to select a carboxyl-protecting group which can be both introduced and removed under sufficiently mild conditions so as not to disrupt the sensitive β-lactam ring system.

One carboxyl-protecting group which has been extensively described in the literature is the methoxymethyl ester group ($-COOCH_2OCH_3$). This ester has been found to be generally applicable as a protecting group for the 3-carboxylic acid group of a penicillin or the 4-carboxylic acid group of a cephalosporin (see, for example, U.S. Pat. Nos. 3,996,236, 3,843,639, 4,125,716 and references cited therein).

In addition to their use as intermediates for the preparation of biologically active penicillin and cephalosporin antibiotics, the methoxymethyl esters of at least certain penicillins and cephalosporins have been reported to be useful antibiotics per se, said esters being physiologically cleaved in the body to give improved blood levels and/or different tissue distribution of antibiotic compared to the corresponding unesterified compounds [see, for example, U.S. Pat. Nos. 3,996,236 (methoxymethyl ester of hetacillin) and 4,125,716 (methoxymethyl esters of hetacephalexin and hetacefadroxil)].

Preparation of methoxymethyl esters of penicillins and cephalosporins has generally been carried out with halomethyl methyl ethers such as chloromethyl methyl ether (see, for example, U.K. Pat. No. 1,488,308). Recent severe occupational restrictions on the use of chloromethyl methyl ether [Fed. Regist. 39, § 1910, 93h (Jan. 29, 1974)] due to its known carcinogenicity have produced a need for a suitable substitute for the halomethyl methyl ether reagents.

Several literature references have recently appeared describing the use of dimethoxymethane (methylal) in methoxymethylation reactions, e.g. Synthesis, August 1977, page 567; Synthesis, April 1975, page 276; Synthesis, April 1976, page 244. From the disclosed conditions and reagents required in such processes, however, it is clear that these processes are too drastic for the relatively unstable penicillin and cephalosporin molecules.

Other literature reveals the preparation (from methylal) and use of methoxymethyl methanesulfonate (J. Am. Chem. Soc., 91, 5663 (1969); U.S. Pat. No. 3,737,447). This reagent is reported to be useful as an oxyalkylating agent for ether formation. From the tremendous reactivity indicated in the J. Am. Chem. Soc. paper, it is clear that use of methoxymethyl methanesulfonate for introducing $-CH_2OCH_3$ on a carboxylic acid group of an unstable molecule such as a penicillin or cephalosporin was not contemplated.

It was an object of the present invention to provide a new method for preparing methoxymethyl esters of penicillins and cephalosporins in high yield without use of a halomethyl methyl ether esterifying agent and without destruction of the sensitive β-lactam ring system. Still other objects and features of the invention will become apparent from the following description.

SUMMARY OF THE INVENTION

The present invention provides an improved process for esterifying the 3-carboxyl group of a penicillin or the 4-carboxyl group of a cephalosporin to form a methoxymethyl ester group, which process comprises reacting the penicillin or cephalosporin free acid or a carboxylic acid salt thereof with methoxymethyl methanesulfonate as the esterifying agent in the presence of base.

Methoxymethyl methanesulfonate is a known reagent and its preparation has been disclosed in the literature, e.g. in U.S. Pat. No. 3,737,447. While it has previously been disclosed as being useful for ether formation, N-alkylation and C-alkylation, it has not been reported to have utility as an esterifying agent. The extreme reactivity of the reagent, moreover, would lead one away from employing it in esterification of unstable carboxylic acids such as penicillins and cephalosporins.

Contrary to what might be expected, we have found that methoxymethyl methanesulfonate may be successfully used to esterify the carboxyl group of organic carboxylic acids (including unstable acids) so as to form the corresponding methoxymethyl ester group. While the process is generally applicable for esterification of the carboxyl group of any carboxylic acid, it is particularly valuable in esterifying the 3-carboxyl group of a penicillin or the 4-carboxyl group of a cephalosporin.

In the preferred aspect of the present invention, i.e. the methoxymethylation of a penicillin 3-carboxyl group or a cephalosporin 4-carboxyl group, the particular penicillin or cephalosporin used as the starting material is not critical since the reaction is concerned only with esterification of the 3- or 4-carboxyl portions of the β-lactam molecule. When the starting material contains a substituent which may be influenced in the course of the esterification such as amino, hydroxyl or carboxyl, such substituent may if desired be protected prior to the methoxymethylation reaction by conventional protecting groups. Alternatively, said substituent may be left unprotected and may be allowed to react with the esterifying agent. Since the desired 3- or 4- carboxyl group is still successfully esterified, however, such side reactions do not affect the intended reaction and the overall esterification process is within the scope of the present invention.

The term "penicillin" as used herein is meant to include 6-aminopenicillanic acid (6-APA), 6-aminopenicillanic acid 1-oxide (6-APA sulfoxide) and derivatives of 6-APA or 6-APA sulfoxide having a conventional penicillin side chain in the 6-position. Thus, the penicillin starting material may have the general formula

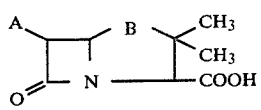

wherein B is =S or =S—O and A is NH₂ or a conventional penicillin side chain.

The term "cephalosporin" as used herein is meant to include all known cephalosporin compounds including especially those of the general formula

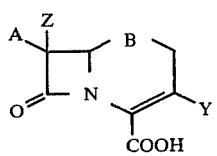

wherein B is =S or =S—O, A is NH₂ or a conventional cephalosporin side chain, Z is hydrogen or methoxy and Y is a conventional 3-substituent of a 3-cephem nucleus.

Substituent A in starting materials II and III above may be any conventional side chain previously disclosed for use as a penicillin 6-substituent or a cephalosporin 7-substituent. The nature of the A substituent is not critical for carrying out the esterification process of the present invention, but such substituent will normally be one which has been found to impart useful biological activity to a penicillin or cephalosprin nucleus. In addition to NH₂, A may thus be acylamino such as is present in one of the reported natural or semi-synthetic penicillins or cephalosporins. Included within acylamino are sidechains wherein an acylamino group having a free amino group, preferably an α-amino group, is reacted with an aldehyde or ketone such as formaldehyde, acetaldehyde or acetone. A preferred group of this type has the formula

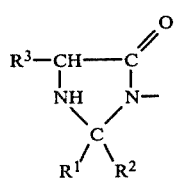

wherein either $R^1$ and $R^2$ are each methyl or $R^1$ is hydrogen and $R^2$ is methyl and wherein $R^3$ is cyclohexadienyl, 2- or 3-thienyl, phenyl or phenyl substituted by one or more, preferably one or two, of the substituents selected from halo (chloro, bromo, fluoro, iodo), hydroxy, $C_1$–$C_6$ alkyl, nitro, amino, $C_1$–$C_6$ alkanoyl, $C_1$–$C_6$ alkanoyloxy, trifluoromethyl, $C_1$–$C_6$ alkoxy, $C_1$–$C_6$ alkanoylamino or $C_1$–$C_6$ alkylthio. Most preferred members of this group are those wherein $R^3$ is phenyl or p-hydroxyphenyl and $R^1$ and $R^2$ are each methyl.

Examples of suitable A substituents are provided in U.K. Pat. No. 1,525,626 (see definition of $R^1$—NH) and in U.S. Pat. No. 4,112,230 (columns 5–16 under definition of R—NH). Illustrative of such substituents are those of the formulae:

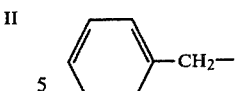

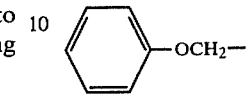

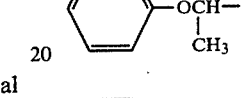

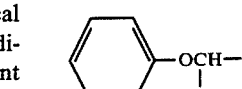

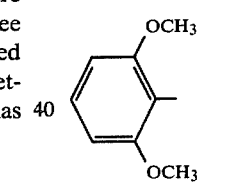

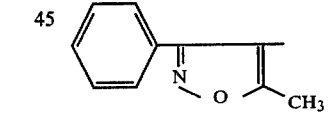

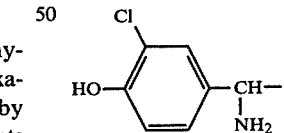

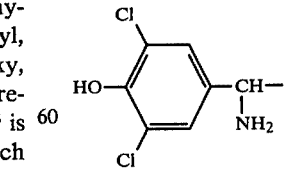

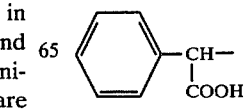

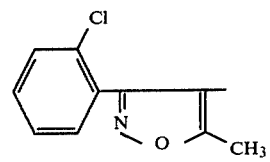

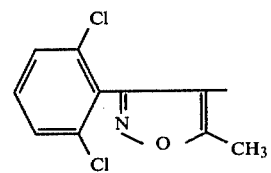

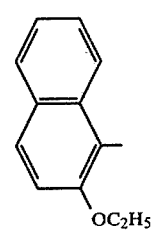

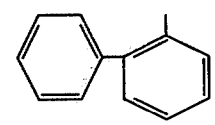

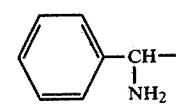

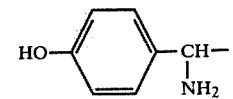

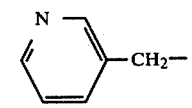

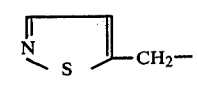

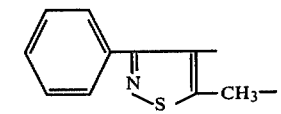

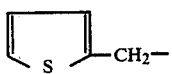 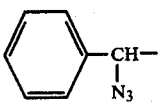 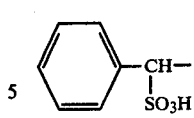 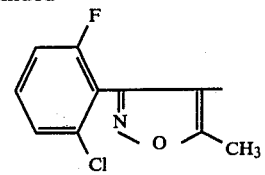

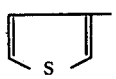 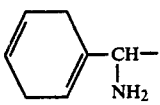 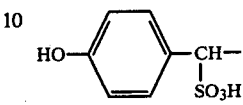 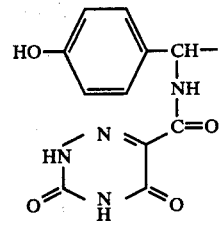

 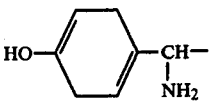 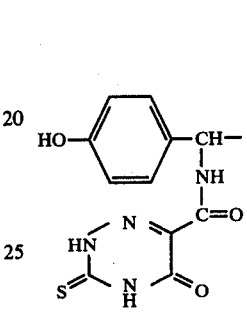 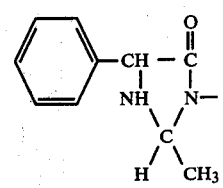

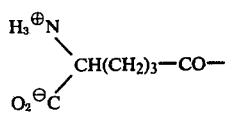 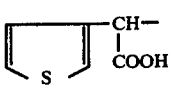 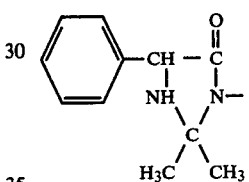 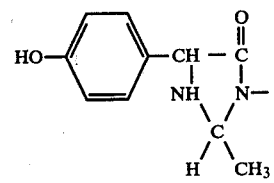

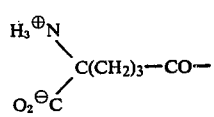  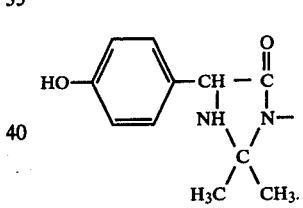

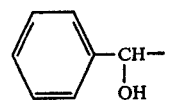 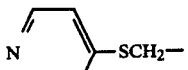

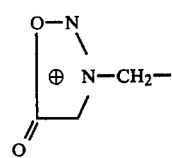 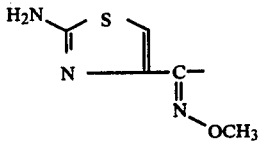

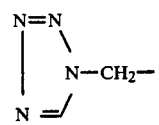 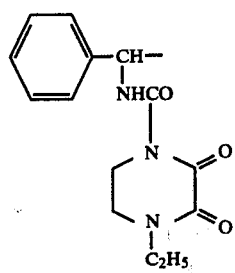

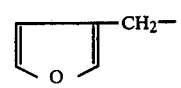 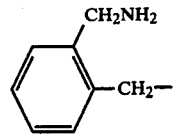

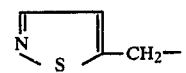 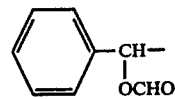

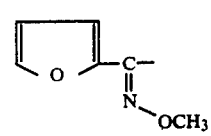 

As substituent Y on the cephalosporin starting material, there may be used any conventional 3-substituent for a 3-cephem nucleus. As examples, Y may be hydrogen, halo (Cl, Br, I, F), $CH_3$, $-CH_2OH$, $-CH_2OCOCH_3$, $-CH_2OCH_3$, $-CH_2SCH_3$,

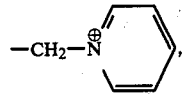

$-CH_2OCONH_2$, $-CH_2SC_6H_5$, $-CH_2N_3$,

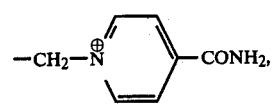

$-CH_2OCON(CH_3)_2$, $-CH_2NH_2$ or $-SHet$ in which Het represents an optionally substituted 5- or 6-membered heterocyclic ring containing 1–4 atoms selected from N, O and S, the substituents on said ring being preferably one or two radicals selected from halo, $C_1$–$C_4$ alkyl, $C_1$–$C_4$ alkoxy, cyano, carboxyl, amino, nitro, trifluoromethyl, hydroxy, hydroxymethyl, $C_1$–$C_4$ alkylthio, $C_1$–$C_4$ alkylamino, di($C_1$–$C_4$)alkylamino, mercapto, phenyl, benzyl, di($C_1$–$C_4$)alkylamino($C_1$–$C_4$)alkyl, —$(CH_2)_n COOH$ and —$(CH_2)_n SO_3 H$ wherein n is an integer from 1 to 4. As examples of suitable heterocyclic rings there may be mentioned thienyl, furyl, pyrazolyl, imidazolyl, isoimidazolyl, triazolyl, tetrazolyl, thiazolyl, thiadiazolyl, oxazolyl, oxadiazolyl, isothiazolyl, isoxazolyl, pyridyl, pyridazinyl, pyrazinyl, pyrimidinyl and triazinyl. Especially preferred Het groups are 1,2,3-triazolyl, 2-methyl-1,3,4-thiadiazol-5-yl, 2-methyl-1,3,4-oxadiazol-5-yl, 1-N-methyltetrazolyl, 1-carboxymethyl tetrazol-5-yl and 1-carboxyethyl-tetrazol-5-yl. Typical S-Het groups would include those such as

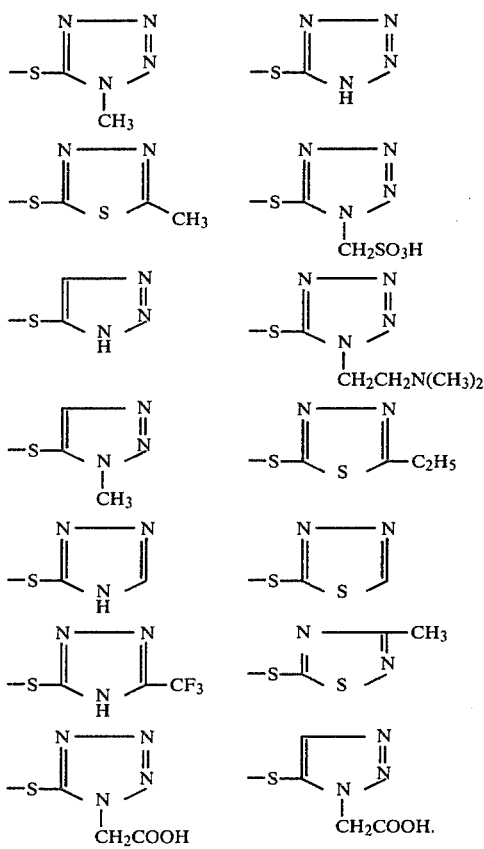

Since methoxymethyl esters are reported to be particularly useful for those penicillins and cephalosporins which are orally administered, a preferred group of starting materials for use in the present process comprises ampicillin, amoxicillin, hetacephalexin, hetacefadroxil, hetacephaloglycin, oxacillin, cloxacillin, dicloxacillin, flucloxacillin, hetacillin, metampicillin, hetaamoxicillin, cefaclor, nafcillin, meta-chlorocefadroxil, cephradine, cephalexin, cefadroxil, phenoxymethyl penicillin, phenethicillin, propicillin and phenbenicillin.

For use as intermediates, methoxymethyl esters may in general be made of any penicillin containing a 3-carboxyl group or any cephalosporin containing a 4-carboxyl group. Illustrative of such starting materials are 6-APA, 6-APA sulfoxide, 7-ACA, 7-ADCA, cephalosporin C, cephalosporin D, benzylpenicillin, methicillin, carbenicillin, cephalothin, cephaloridine, ticarcillin, cefaparole, cefatrizine, cefamandole, cefazaflur, ceforanide, cephapirin, cefoxitin, cefuroxime, cefazolin, cefotaxamine and pipericillin.

In the esterification process of the present invention, a penicillin containing a 3-carboxylic acid group or a cephalosporin containing a 4-carboxylic acid group is reacted in the form of the free acid or as a carboxylic acid salt thereof with methoxymethyl methanesulfonate as the esterifying agent in a substantially anhydrous inert organic solvent and in the presence of base.

Because of the extreme sensitivity of methoxymethyl methanesulfonate to water, the esterification reaction is preferably carried out in an anhydrous or substantially anhydrous inert organic solvent such as methylene chloride, acetone, methyl isobutyl ketone, acetonitrile, dimethylformamide, dimethylsulfoxide, chloroform, carbon tetrachloride, ethylene chloride or ethyl acetate. The most preferred solvent is dry methylene chloride.

The reaction proceeds most advantageously when carried out in the presence of a molar excess of an organic or inorganic base such as an alkali metal hydroxide, carbonate or bicarbonate, an alkaline earth metal hydroxide, carbonate or bicarbonate or an organic amine. Examples of suitable bases are NaOH, Ca(OH)$_2$, Mg(OH)$_2$, NaHCO$_3$, K$_2$CO$_3$, pyridine, triethylamine, trimethylamine, tributylamine, diethylamine, dicyclohexylamine, N-ethylpiperidine, N-methylpiperidine, N-methylmorpholine, etc. Most preferably an organic amine base such as triethylamine is employed.

As mentioned above, the penicillin or cephalosporin starting material may be used in the form of the carboxylic acid or as a salt of the carboxylic acid such as an alkali metal, alkaline earth metal or amine salt. When the free acid is employed a salt is formed in situ upon addition of the base to the reaction mixture.

Temperatures during the esterification are not critical and may vary from about −20° C. to about +50°C. Best results, however, are generally achieved at temperatures below room temperature, preferably in the range of about −10° to +10° C.

The methoxymethyl methanesulfonate is generally used in a molar excess relative to the penicillin or cephalosporin starting material. Acidic impurities (mainly methanesulfonic acid) generally present at least to some degree in the methoxymethyl methanesulfonate are neutralized during the reaction by the base which also serves as a solubilizing agent for the β-lactam starting materials.

Following formation of the desired methoxymethyl ester, the product is recovered by conventional procedures.

Preparation of methoxymethyl esters of penicillins or cephalosporins containing 6- or 7- side chains of the type

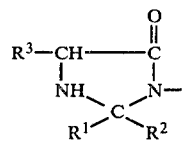

may be accomplished by reaction of the appropriate penicillin or cephalosporin acid or salt with methoxymethyl methanesulfonate as described above. Alternatively, the corresponding α-amino starting material having the side chain

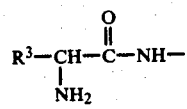

may be esterified with the methoxymethyl methanesulfonate in the presence of the appropriate aldehyde or ketone (e.g. acetaldehyde or acetone) so as to form both the desired ester and sidechain in one step.

The process of the present invention has been found to give good quality product in high yields with a wide variety of penicillin and cephalosporin starting materials. Because of the restrictions on use of chloromethyl methyl ether, the esterifying agent previously used to form methoxymethyl esters of unstable β-lactam acids, the present process is believed to represent a useful and commercially feasible alternative to the prior halomethyl methyl ether process.

The following examples are given solely for purposes of illustration and not of limitation.

PREPARATION OF STARTING MATERIALS

1. Acetyl Methanesulfonate

A. From Acetic Anhydride

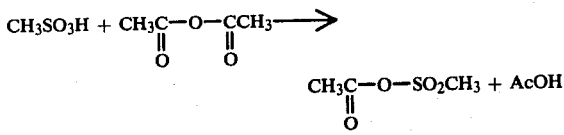

Materials:

| | | |
|---|---|---|
| CH$_3$SO$_3$H (98%) | 30.0 g. | 0.312 mole |
| Ac$_2$O | 60 ml. | 0.740 mole |

Procedure:
1. Equip a 3-neck flask with stirrer, thermometer, N$_2$ bleedtube and distilling head connected to condenser and receiving flask.
2. Add the methanesulfonic acid and cool to ~10° under N$_2$.
3. Add the acetic anhydride with stirring over 5 min.
4. Remove cooling and stir 15 min.
5. Apply a vacuum of ~2 mm and warm the flask (oil bath 30°–40°) while cooling receiving flask to about −50°.
6. Increase vacuum, as fast as possible without excessive bumping to the maximum vacuum possible.
7. Continue the evaporation until 45–50 ml. of condensate has been collected (~2 hrs).
8. Check the residual, pale-yellow oil, (41.0, 95%) by NMR[1,2].
9. Distill the residue under high vacuum (BP 55°–58°, 10$^{-2}$ mm) to give 34.8 g. (85% recovery) of mixed anhydride.

Notes:
1. NMR (CDCl$_3$): δ, 2.3 (COCH$_3$), 3.3 (SO$_2$CH$_3$). The NMR of this crude material, always shows some Ac$_2$O-AcOH, however this does not seem to cause any problems in the subsequent reactions.
2. This crude material can be used as such without any decrease in yield of the ester product.
3. The product should be stored under N$_2$ and kept refrigerated (<10° C.) if not used immediately.

B. From Acetyl Chloride

The mixed anhydride can also be prepared by refluxing a solution of methanesulfonic acid (30.0 g., 0.31 mole) and acetyl chloride (75 ml., 1.1 mole) for 3–4 hrs., purging the reddish solution with N$_2$ bubbling for 16 hrs. and removing excess AcCl under reduced pressure, leaving a dark-red residue (40.9 g., 95%). When this material is free of dissolved HCl (which is sometimes stubbornly retained) it gives the same results, as the crude material prepared from the acetic anhydride route, in the preparation of the ester products.

2. Methoxymethyl Methanesulfonate-generated in situ from acetyl methanesulfonate and methylal In a flame dried 3-neck flask under nitrogen atmosphere, acetyl methanesulfonate (16 g., 0.115 mole) was dissolved in chloroform (30 ml.). The solution was first cooled to −15° C. then methylal (10.2 ml., 0.115 mole) was added dropwise over 15 min. Stirring was continued at −15° C. for 10 min., then the cooling bath was removed and stirring was continued for 15–20 minutes more. The reagent is ready for use at this point and its purity is checked by NMR (CHCl$_3$) spectroscopy.

EXAMPLE 1

Methoxymethyl Ester of Heta-amoxicillin

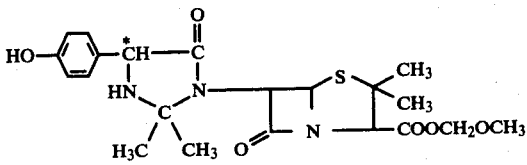

Pulverized heta-amoxicillin (35 g.; 0.086 mole) was suspended in methylene chloride (150 ml.) and acetone (15 ml.) at 0° C. With mechanical stirring, triethylamine (13 g.; 0.129 mole) was added dropwise over 10 minutes (keeping pH below 9.4). As soon as a solution was obtained, the "in situ" generated methoxymethyl methanesulfonate (Preparation 2 above) was added dropwise through a dropping funnel at 0° C. over 15 minutes. The reaction mixture was stirred for 0.5 hour at 0° C. and then cold water (150 ml., 0° C.) was added slowly over 5 minutes followed by addition of heptane (150 ml.) over 5 minutes with vigorous stirring (final pH 7.2). After 2 minutes the crystalline product that was suspended between the two layers was filtered and washed with water (70 ml., cooled to 0° C.). The product was vacuum dried at 23° C. to constant weight (30.0 g., 77% yield) and was found to be identical to that obtained by the chloromethyl methyl ether route.

EXAMPLE 2

Methoxymethyl Ester of Heta-amoxicillin

I. Materials

| | Wt. or volume | Moles |
|---|---|---|
| Methoxymethyl methanesulfonate | 33.3 g. | 0.24 mole |
| Methylal | 18.3 g. | 0.24 mole |
| Chloroform (anhydrous) | 60 ml. | |
| Methylene chloride (anhydrous) | 300 ml. | |
| Acetone (anhydrous) | 30 ml. | |
| Heta-amoxicillin | 70 g. | 0.17 mole |
| Triethylamine (anhydrous) | 26.0 g. | 0.26 mole |

| | Wt. or volume | Moles |
|---|---|---|
| Heptane | 300 ml. | |

II. Procedure

1. Add chloroform (60 ml.) and acetyl methanesulfonate[1] (33.3 g., 0.24 mole) to a dry 3-neck flask (250 ml.)
2. Cool contents to −15° C. and then add methylal (18.3 g., 0.24 mole) dropwise at such a rate to maintain the temperature between −10° to −15° C.
3. Discontinue the cooling and continue stirring for 30 minutes more under nitrogen[2].
4. Charge a 3-neck flask (2 l) with dry methylene chloride (300 ml.) and acetone (30 ml.) and cool to 0° C.
5. Suspend pulverized heta-amoxicillin (70.0 g., 0.17 mole) in cold solution.
6. Add triethylamine (26.0 g., 0.26 mole) dropwise (10 min.) and stir until solution is obtained (~5 min.).
7. Add the methoxymethyl methanesulfonate solution from step 3 dropwise over 15 min. under nitrogen atmosphere.
8. Stir the reaction mixture for 30 min. at 0° C.
9. Slowly add cold water (300 ml.) followed by heptane (300 ml.) dropwise over 5 min. with vigorous stirring.
10. Stir the precipitate for 2–3 min., then filter and wash with cold water (100 ml.).
11. Dry product in vacuum oven until constant weight (59.7 g., 77% yield). Check purity by NMR spectroscopy and bio-potency.

Notes:
1.
(a) Acetyl methanesulfonate is available commercially from Chemical Dynamics Corporation of New Jersey U.S.A. and it is listed in the Chemical Sources Europe with the following company names as suppliers:
Aldrich Europe—Jensen Pharmaceuticals
Chemie K.G.—Keppler * Reif.
Interchim.
(b) Undistilled acetyl methanesulfonate prepared from methanesulfonic acid and acetyl chloride or acetic anhydride can also be used.
2. The reagent is very sensitive to moisture. The purity can be checked by NMR spectroscopy using the chloroform solution directly $\delta 3.1$ ($SO_2\underline{CH}_3$); 3.6 ($O\underline{CH}_3$); 5.35 ($O\underline{CH}_2O$). The reagent methoxymethyl methanesulfonate is also available commercially from Chemical Dynamics Corporation of New Jersey U.S.A.

EXAMPLE 3

Methoxymethyl Ester of Hetacillin

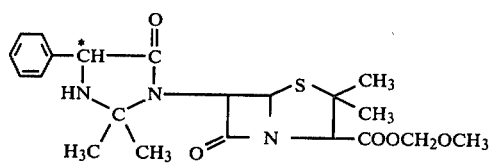

Substitution in the procedure of Example 1 or Example 2 of an equimolar amount of hetacillin for the heta-amoxicillin used therein gives the title product.

EXAMPLE 4

If the general procedure of Examples 1–2 is repeated with the heta-amoxicillin used therein replaced with an equivalent amount of one of the penicillins or cephalosporins listed below, there is produced the corresponding methoxymethyl ester product.

penicillin V
7-phenoxyacetamido-3-methylceph-3-em-4-carboxylic acid
cephalosporin D (N-carbisobutoxy cephalosporin C)
cefazolin
penicillin V sulfoxide
6-aminopenicillanic acid
6-aminopenicillanic acid sulfoxide
ampicillin
amoxicillin
hetacephalexin
hetacefadroxil
hetacephaloglycin
oxacillin
cloxacillin
dicloxacillin
flucloxacillin
cefadroxil
metampicillin
cefaclor
nafcillin
meta-chlorocefadroxil
cephradine
cephalexin
phenethicillin
propicillin
phenbenicillin
7-aminocephalosporanic acid
7-aminocephalosporanic acid sulfoxide
7-aminodeacetoxycephalosporanic acid
cephalosporin C
benzylpenicillin
methicillin
carbenicillin
cephalothin
cephaloridine
ticarcillin
cefaparole
cefatrizine
cefamandole
cefazaflur
ceforanide
cephapirin
cefoxitin
cefuroxime
cefotaxamine
pipericillin
7-methoxycephalosporin C
7-(2,2,-dimethyl-5-oxo-4-[2′-thienyl]-1-imidazolidinyl)-cephalosporanic acid
cephalosporin $C_A$

We claim:
1. In the process for esterifying the 3-carboxyl group of a penicillin or the 4-carboxyl group of a cephalosporin to form a methoxymethyl ester group, the improvement of carrying out the esterification by reaction of the penicillin or cephalosporin free acid or a carboxylic acid salt thereof with methoxymethyl methanesulfonate as the esterifying agent in a substantially anhydrous inert organic solvent in the presence of base and at a temperature of from about −20° C. to about +50° C.

2. The process according to claim 1 wherein the β-lactam starting material is hetacillin or heta-amoxicillin.

3. A process for preparing the methoxymethyl ester of hetacillin which comprises the consecutive steps of
(a) dissolving hetacillin in a mixture of a dry inert organic solvent and acetone by addition of triethylamine at a temperature of from −10° to +10° C.
(b) reacting a solution of methoxymethyl methanesulfonate in a dry inert organic solvent with the solution prepared in step (a) at a temperature of from −10° to +10° C.; and
(c) recovering the methoxymethyl ester of hetacillin from the reaction mixture.

4. A process for preparing the methoxymethyl ester of heta-amoxicillin which comprises the consecutive steps of
(a) dissolving heta-amoxicillin in a mixture of a dry inert organic solvent and acetone by addition of triethylamine at a temperature of from −10° C. to +10° C.;
(b) reacting a solution of methoxymethyl methanesulfonate in a dry inert organic solvent with the solution prepared in step (a) at a temperature of from −10° to +10° C.; and
(c) recovering the methoxymethyl ester of heta-amoxicillin from the reaction mixture.

* * * * *